US00PP34499P3

(12) United States Plant Patent
Koot

(10) Patent No.: US PP34,499 P3
(45) Date of Patent: Aug. 16, 2022

(54) ***BUDDLEJA* PLANT NAMED 'BOTEX 002'**

(50) Latin Name: *Buddleja davidii*
Varietal Denomination: 'Botex 002'

(71) Applicant: Botanic Experience B.V., Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 17/556,977

(22) Filed: Dec. 20, 2021

(65) Prior Publication Data

US 2022/0225553 P1 Jul. 14, 2022

(30) Foreign Application Priority Data

Jan. 13, 2021 (QZ) ..... PBR 20203388

(51) Int. Cl.
*A01H 6/00* (2018.01)
*A01H 5/02* (2018.01)

(52) U.S. Cl.
USPC ..... Plt./242

(58) Field of Classification Search
USPC ..... Plt./242
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Buddleja* plant named 'Botex 002' that is characterized by its dense, compact, somewhat spreading and upright-rounded plant habit, its flowers that are light lilac purple in color, its very floriferous blooming habit, its flowers that have a pleasant fragrance, and its inflorescences and flowers that are large in size.

2 Drawing Sheets

Botanical classification: *Buddleja davidii.*
Variety denomination: 'Botex 002'.

CROSS-REFERENCE TO RELATED APPLICATIONS

This application claims priority to European Community Plant Variety Office (CPVO) Plant Breeder's Rights Application No. 2020/3388 filed on Jan. 13, 2021, under 35 U.S.C. 119(f), the entire contents of which is incorporated by reference herein. This application is also co-pending with a U.S. Plant Patent Application filed for a plant derived from the same breeding program from the same parentage that is entitled *Buddleja* Plant Named 'Botex 001' U.S. Plant application Ser. No. 17,556,969.

BACKGROUND OF THE INVENTION

The present invention relates to a new and distinct cultivar of *Buddleja davidii* and will be referred to hereafter by its cultivar name, 'Botex 002'. 'Botex 002' is a new shrub grown for use as an ornamental landscape plant.

The new cultivar of *Buddleja* is a selection from an ongoing breeding program conducted by the Inventor in Kaatsheuvel, The Netherlands with the objective of creating new cultivars of *Buddleja* with very neat and compact plant habits combined with unique flower colors and floriferous blooming habits.

The Inventor made a cross in summer of 2018 between unnamed and unpatented proprietary plants in the Inventor's breeding program; reference no. 11013 as the female parent and reference no. 263 as the male parent. The Inventor selected 'Botex 002' in summer of 2019 as a single unique plant amongst the seedlings that resulted from the above cross.

Asexual propagation of the new cultivar was first accomplished by the Inventor using stem cuttings in Kaatsheuvel, The Netherlands in August of 2019. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Botex 002' as a unique cultivar of *Buddleja.*

1. 'Botex 002' exhibits a dense, compact, somewhat spreading and upright-rounded plant habit.
2. 'Botex 002' exhibits flowers that are light lilac purple in color.
3. 'Botex 002' exhibits a very floriferous blooming habit.
4. 'Botex 002' exhibits flowers that have a pleasant fragrance.
5. 'Botex 002' exhibits inflorescences and flowers that are large in size.

The female parent of 'Botex 002' differs from 'Botex 002' in having inflorescences that are much shorter in length, flowers that are smaller in size with purple centers, and in having a more compact plant habit. The male parent of 'Botex 002' differs from 'Botex 002' in having inflorescences that are more narrow with smaller flowers that are very dark purple in color. 'Botex 002' can be compared to the *Buddleja* cultivars 'Nanho Blue' (not patented) and 'Botex 001'. 'Nanho Blue' differs from 'Botex 002' in having a taller plant height, longer branches, inflorescences that are longer and thicker in size, and individual flowers that are larger in size. 'Botex 001' differs from 'Botex 002' in having smaller inflorescences with flowers that are intense purple in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Podoslonami, Groen Vandaag, Plantago, Greenport, Gabot, Bloemenkrant, Floricade, Plamntipp, Hortipoint, CG Concept, Stad+Groen, Floranews, Tuinzaken, Handel & Techniek, Van Son & Koot BV, KVBC, Perishablenews, Hortweek, Buddlejagarden, Boom-in-Business, Greenity, and Obst & Garden.

BRIEF DESCRIPTION OF THE DRAWINGS

The accompanying color photographs illustrate the overall appearance and distinct characteristics of the new *Buddleja*. The photographs were taken of a plant about 3 years in age as grown outdoors in a trial garden in Kaatsheuvel, The Netherlands.

The photograph in FIG. 1 provides a side view of the overall plant habit of 'Botex 002' in bloom.

Figure 1:
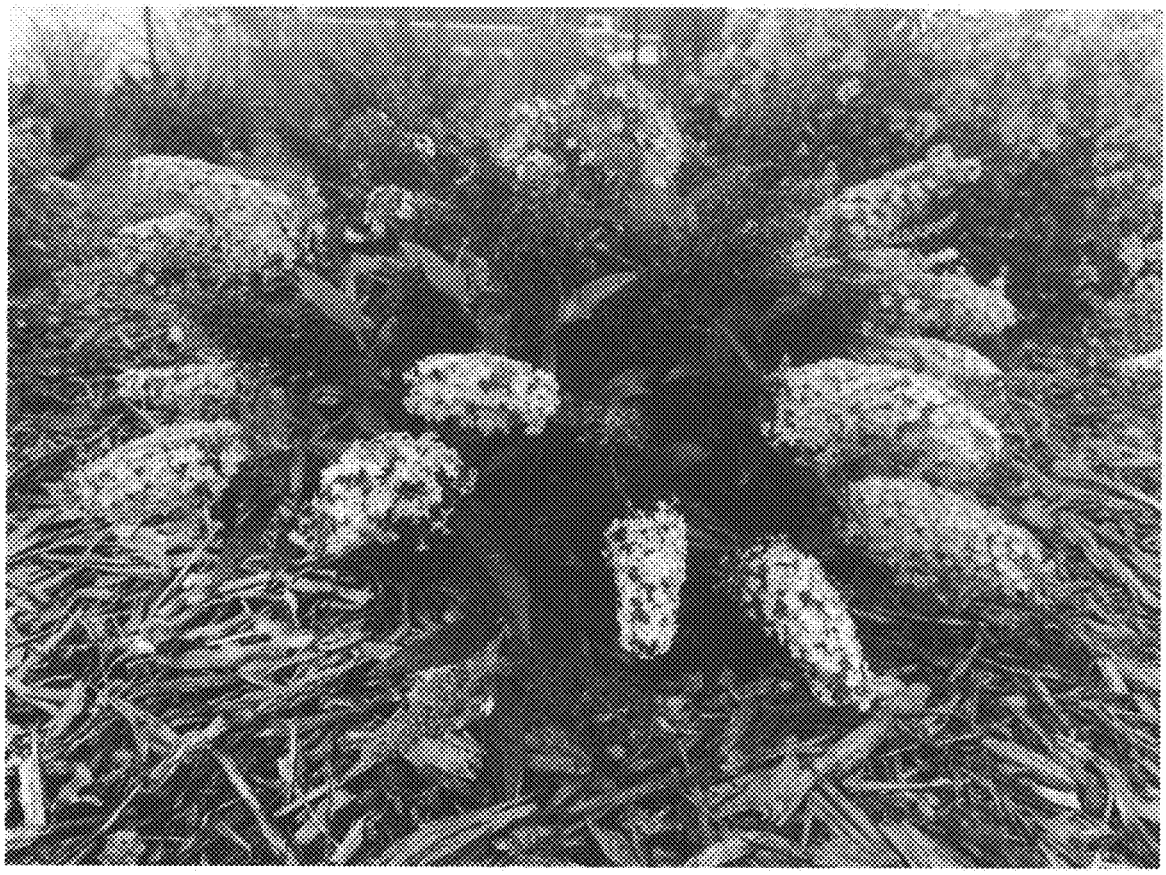
Figure 2:
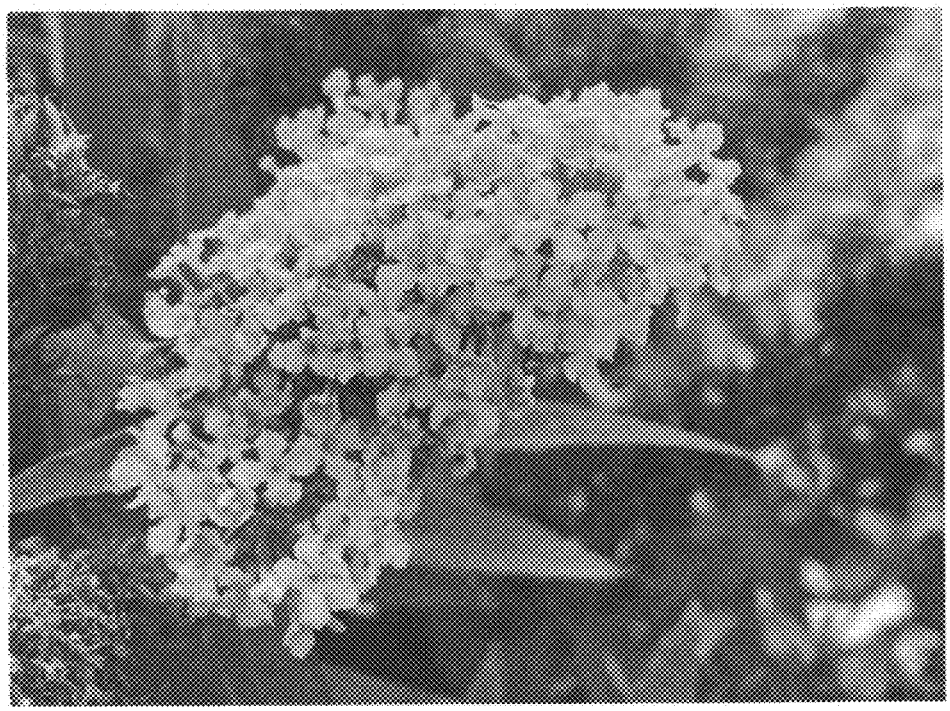

The photograph in FIG. 2 provides a close-up view of an inflorescence of 'Botex 002'.

Figure 3:
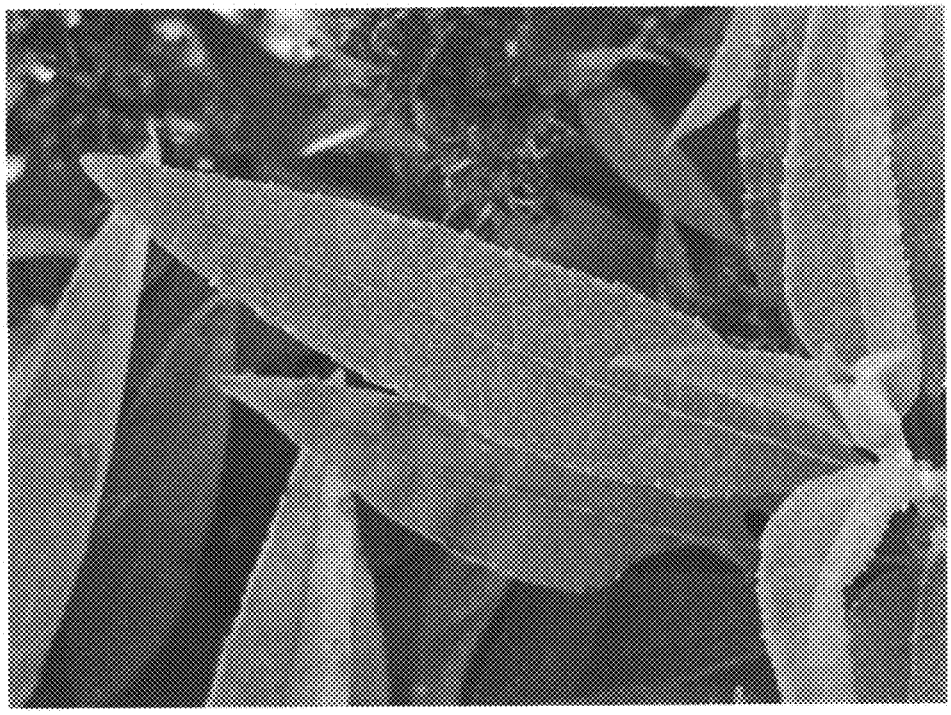

The photograph in FIG. 3 provides a close-up view of the foliage of 'Botex 002'.

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of one-year-old plants as grown in a greenhouse in 19-cm containers in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—July to October in The Netherlands.

*Plant type.*—Deciduous perennial shrub.

*Plant habit.*—Dense, compact, somewhat spreading and upright-rounded.

*Plant size.*—An average of 60 cm in height and 36 cm in width as a one-year-old plant and reaches 80 cm in height and 80 to 90 cm in spread as grown in the landscape.

*Cold hardiness.*—At least in U.S.D.A. Zone 5.

*Diseases and pests.*—No susceptibility and resistance to diseases or pests has been observed.

*Propagation.*—Stem cuttings.

*Root description.*—Fibrous.

*Root development.*—An average of 8 weeks to initiate roots and eight weeks to fully root as a young plant in a P9 container.

*Growth rate.*—Vigorous.

Branch description:

*Branch shape.*—Quadrangular.

*Branch color.*—Young stems; 145B, mature stems; 199A.

*Branch strength.*—Strong.

*Branch size.*—An average of 22 cm in length and 5 mm in diameter.

*Branch surface.*—Pubescent.

*Branch internode length.*—Average of 2.2 cm.

*Branching.*—1 main branch, 4 lateral branches.

Foliage description:

*Leaf shape.*—Narrowly elliptical to elliptical.

*Leaf division.*—Simple.

*Leaf base.*—Attenuate.

*Leaf apex.*—Acute.

*Leaf fragrance.*—None.

*Leaf venation.*—Pinnate, color; upper surface 144A, lower surface 191D, main vein 145B.

*Leaf margins.*—Serrate.

*Leaf arrangement.*—Opposite.

*Leaf attachment.*—Petiolate.

*Leaf surface.*—Both sides are smooth and matte, lower surface pubescent.

*Leaf size.*—An average of 11 cm in length and 3.1 cm in width.

*Leaf quantity.*—An average of 8 per stem.

*Leaf color.*—Young upper surface; 137C, base 145C, young lower surface; 191A, mature upper surface; 137A, mature lower surface; 191D.

*Petioles.*—An average of 5 mm in length and 2 mm in diameter, medium to high strength, both surfaces 145B in color, upper surface smooth and glabrous, lower surface slightly pubescent.

Inflorescence description:

*Inflorescence type.*—Compound terminal and axial panicles.

*Inflorescence size.*—An average of 11.5 cm in height, 6.5 cm in width.

*Flower fragrance.*—Sweet, pleasant and medium strength.

*Lastingness of flowers.*—An average of 5 days, persistent, inflorescence is semi-indeterminate.

*Flower buds.*—Oblong, average of 6 mm in length and 1 mm in diameter, 83A in color.

*Flower aspect.*—Upright.

*Flower quantity.*—An average of 150 flowers per inflorescence.

*Flower type.*—Single, salverform.

*Flower surface.*—All surfaces glabrous and smooth.

*Flower size.*—An average of 9 mm in height, 1.2 cm in depth, flower throat; 4 mm in length, 1 mm in diameter, flower tube; 3 mm in length, 1 mm in diameter.

*Peduncles.*—An average of 2 cm in length and 2.5 mm in diameter, held erect, 145A in color, strong, glossy and pubescent surface.

*Pedicels.*—An average of 2 mm in length and 1 mm in diameter, held at an average angle of 45°, 145B in color, strong, surface is glossy and pubescent.

*Calyx.*—Campanulate in shape, an average of 2 mm in depth and 1 mm in diameter.

*Sepals.*—4, 1 whorl, rotate arrangement, fused into a campanulate shape, 2 mm in length, 1.5 mm in width, lanceolate in shape, acute apex, fused base, entire margin, both surface are matte and slightly pubescent, color; when opening and fully open upper and lower surface 145A.

*Petals.*—Average of 4, rotate, fused into salverform, 1 whorl, roughly spathulate in shape, slightly undulate margin, rounded apex, an average of 3 mm in length and width, outer and inner surface is glabrous, velvety and matte, color; upper and lower surface when opening and fully open N87D, center 23A, center 23A, flower throat N87D, flower tube 21B, base N87D.

Reproductive organs:

*Gynoecium.*—1 pistil, 3 mm in length, style; an average of 2 mm in length, 145D in color, stigma; elongated, 1 mm in length and 145B in color, ovary is 145D in color.

*Androcoecium.*—Stamens; 4, filament; 4 mm in length and 20B in color, anther; ovate in shape, 1 mm in length, 11D in color, pollen; low in quantity, 11D in color.

*Fruit and seed.*—No seeds or fruit observed to date.

It is claimed:

1. A new and distinct cultivar of *Buddleja* plant named 'Botex 002' as herein illustrated and described.

* * * * *